(12) United States Patent
Hofmann et al.

(10) Patent No.: US 8,063,640 B2
(45) Date of Patent: Nov. 22, 2011

(54) METHOD AND DEVICE FOR MEASURING A SAMPLE IN AN NMR SPECTROMETER USING A COUPLING CONFIGURATION WITH A PRESS FIT CELL HAVING A CAPILLARY ENVELOPE FASTENER

(75) Inventors: Martin Hofmann, Rheinstetten (DE); Thorsten Marquardsen, Karlsruhe (DE)

(73) Assignee: Bruker BioSpin GmbH, Rheinstetten (DE)

( * ) Notice: Subject to any disclaimer, the term of this patent is extended or adjusted under 35 U.S.C. 154(b) by 0 days.

(21) Appl. No.: 12/923,321

(22) Filed: Sep. 15, 2010

(65) Prior Publication Data
US 2011/0006770 A1    Jan. 13, 2011

Related U.S. Application Data

(63) Continuation of application No. 11/812,821, filed on Jun. 22, 2007, now abandoned.

(30) Foreign Application Priority Data

Jun. 27, 2006  (DE) .......................... 10 2006 029 496

(51) Int. Cl.
*G01V 3/00* (2006.01)
(52) U.S. Cl. ........................................ 324/321; 324/318
(58) Field of Classification Search .................. 324/321, 324/318
See application file for complete search history.

(56) References Cited

U.S. PATENT DOCUMENTS

| 5,288,113 | A * | 2/1994 | Silvis et al. | 285/342 |
| 6,700,379 | B2 * | 3/2004 | Peck et al. | 324/321 |
| 7,145,340 | B2 * | 12/2006 | Rindlisbacher et al. | 324/321 |
| 7,651,280 | B2 * | 1/2010 | Mueller et al. | 385/92 |

* cited by examiner

*Primary Examiner* — Louis Arana
(74) *Attorney, Agent, or Firm* — Paul Vincent

(57) ABSTRACT

A method for measuring an sample in an NMR spectrometer uses a coupling configuration (1; 30) comprising a coupling element (3) and a supply capillary (2), wherein the coupling element (3) has a funnel-shaped section (5) which clamps an end (6) of the supply capillary (2). An envelope capillary (10) is provided into which the supply capillary (2) is inserted, wherein the end (6) of the supply capillary (2) projects past an end (11) of the envelope capillary (10), and the end (11) of the envelope capillary (10) is also clamped in the funnel-shaped section (5).

8 Claims, 3 Drawing Sheets

METHOD AND DEVICE FOR MEASURING A SAMPLE IN AN NMR SPECTROMETER USING A COUPLING CONFIGURATION WITH A PRESS FIT CELL HAVING A CAPILLARY ENVELOPE FASTENER

This application is a continuation of Ser. No. 11/812,821 filed Jun. 22, 2007 now abandoned and claims Paris Convention priority of DE 10 2006 029 496.3 filed Jun. 27, 2006 the complete disclosures of which are hereby incorporated by reference.

BACKGROUND OF THE INVENTION

The invention concerns a coupling configuration comprising a coupling element and a supply capillary, wherein the coupling element has a funnel-shaped section which clamps an end of the supply capillary.

A coupling means of this type is disclosed in the catalogue of Polymicro Technologies, LLC, PT-MLC/03-02, "Inner-Lok" of 2002.

Capillaries (supply capillaries) are used to supply liquid samples to a measuring apparatus, e.g. a gas chromatography system or an NMR spectrometer. These capillaries are usually produced from fused silica to ensure good chemical resistance of the capillary to the test sample or its solvent. The sample is thereby mostly pushed along by a downstream transport liquid, e.g. pure solvent. The capillaries have a relatively small inner diameter, in most cases in a range below 0.5 mm, in order to also be able to supply small sample amounts.

The construction of a transition from one capillary to another capillary, or another means to which the liquid test sample is to be supplied, is thereby particularly difficult to realize. The capillary is conventionally fixed, e.g. melted, at such transition locations. Mounting is generally quite expensive and time-consuming, and moreover susceptible to damage. If the capillary is damaged, e.g. broken, it must be repaired by experts, which is expensive.

In contrast thereto, so-called "press fit" connections or couplings are very easy to mount. A capillary is thereby inserted into a cone of a coupling element and pressed through the tapering. This type of clamping fixation, which is based on the elastic properties of the capillary, is sufficiently rigid for many applications.

The above-mentioned "inner-lok" is substantially a glass tube whose inner diameter decreases from both openings towards the inside. One capillary can be pushed into each opening, whereby two capillaries can be connected to each other.

This type of mounting, however, bears the danger that the capillary is not sufficiently fixed in the coupling element and might be inadvertently removed from the coupling element. Damage to a capillary, in particular breakage in the vicinity of the coupling element, could also easily happen.

It is therefore the underlying purpose of the present invention to provide a coupling configuration of the above-mentioned type, wherein mounting of the supply capillary in the coupling element is improved, as is protection against capillary breakage.

SUMMARY OF THE INVENTION

This object is achieved by a coupling configuration of the above-mentioned type which is characterized in that an envelope capillary is provided into which the supply capillary is inserted, wherein the end of the supply capillary projects past an end of the envelope capillary, and wherein the end of the envelope capillary is also clamped in the funnel-shaped section.

In the inventive coupling configuration, the supply capillary is secured twice in the coupling element. The end of the supply capillary is clamped directly in the funnel-shaped section after axial insertion, and forms a first holding ring. The end of the supply capillary is thereby slightly elastically compressed in a radial direction, thereby increasing the adhesive or frictional force.

The end of the envelope capillary is moreover clamped between the supply capillary and the funnel-shaped section. The envelope capillary is inserted in an axial direction into the funnel-shaped section after clamping the supply capillary. The envelope capillary (and possibly also the supply capillary) is thereby elastically compressed in a radial direction, thereby producing a second holding ring. The envelope capillary thereby adheres to the funnel-shaped section and the supply capillary adheres to the envelope capillary.

With the double mounting of the supply capillary, the overall mounting in the coupling configuration becomes safer and can withstand, in particular, a higher tensile force and a higher pressure of the supplied liquid compared to conventional single mounting methods.

The envelope capillary moreover mechanically protects the supply capillary. The envelope capillary extends by a certain distance from the coupling element along the supply capillary. The particularly endangered transition area (which is highly susceptible to breakage due to insufficient capillary flexibility in the vicinity of the mounting) is in any event protected by the envelope capillary. The envelope capillary can thereby mechanically support the supply capillary. The envelope capillary typically extends along the supply capillary through at least 2 cm, away from the coupling element. However, the envelope capillary preferably extends substantially along the entire length of the supply capillary.

The envelope capillary preferably tightly abuts the supply capillary, wherein e.g. the inner diameter of the envelope capillary is larger than the outer diameter of the inner capillary by at most 40 µm. The material of the envelope capillary can preferably be easily elastically deformed in order to also ensure good elastic deformability of the bond between the supply and envelope capillaries.

In one particularly preferred embodiment of the inventive coupling configuration, the supply capillary consists of fused silica or polyether etherketone (PEEK) or polytetrafluoroethylene (PTFE). These materials are chemically resistant to many sample substances and solvents.

In one particularly preferred embodiment, the supply capillary has an inner diameter of between 50 µm and 500 µm. The associated outer diameters result from typical supply capillary wall thicknesses of approximately 20 to 100 µm. The protective effect of the envelope capillary is utilized with particular advantage with such supply capillary diameters.

In one further preferred embodiment, the envelope capillary consists of plastic material, in particular PEEK. Plastic materials have good elastic deformation properties.

In another particularly preferred embodiment of the inventive coupling configuration, the envelope capillary is marked at the outside with an indicative color, in particular, yellow, orange or red. This marking may be provided by coloring the whole surface, through stripes, rings or spots. The overall capillary can be perceived more easily due to the indicative color, thereby preventing inadvertent contact with the user. The envelope capillary also increases the diameter of the overall capillary, such that it is more clearly visible to the naked eye.

One particularly preferred embodiment comprises a leakage sensor for monitoring a gap between the supply capillary and envelope capillary, wherein the leakage sensor is preferably disposed between the supply capillary and the envelope capillary. When a liquid, i.e. the test substance or its solvent, enters the space between the envelope capillary and the supply capillary, leakage of the supply capillary or leakage on the funnel-shaped section can be detected before large amounts of sample substance or solvent are lost or escape into the surroundings. This is particularly advantageous for small sample amounts and toxic liquids. The leakage sensor may be provided e.g. in the form of capacitance measurement between two closely arranged plates, or by measuring the conductivity between two closely spaced contacts. The leakage sensor may be disposed in the space (gap) or also outside of the gap, e.g. in case of an opening.

In one particularly preferred embodiment of an inventive coupling configuration, the coupling element has a further funnel-shaped section which clamps one end of a further supply capillary, and a further envelope capillary is provided into which the further supply capillary is inserted, wherein the end of the further supply capillary projects past an end of the further envelope capillary, and the end of the further envelope capillary is also clamped in the further funnel-shaped section. Two capillaries may then be connected to the coupling configuration. The funnel-shaped sections have a connection for the supplied liquid, such that the supply capillary and the further supply capillary are connected to each other.

In a preferred further development of this embodiment, the funnel-shaped section and the further funnel-shaped section are disposed coaxially. This yields a good, in particular, laminar flow behavior of the supplied liquid.

In another preferred further development, the funnel-shaped section and the further funnel-shaped section immediately merge into each other or are connected by an intermediate section whose diameter is smaller or equal to the narrowest diameters of the funnel-shaped sections. This further development is particularly simple but highly suitable to connect two supply capillaries, e.g. in order to lengthen a capillary connection or to repair a broken supply capillary.

In an alternative further development, the funnel-shaped section and the further funnel-shaped section terminate in a cell having a diameter which is larger than the narrowest diameters of the funnel-shaped sections. The cell can be used as a sample space to perform a measuring operation, e.g. spectroscopic measurement. For this reason, the sample volume in the sample space is increased.

The present invention also concerns the use of this further development of an inventive coupling configuration as a measuring cell in a nuclear magnetic resonance (NMR) spectrometer.

Further advantages of the invention can be extracted from the description and the drawing. The features mentioned above and below may be used in accordance with the invention individually or collectively in arbitrary combination. The embodiments shown and described are not to be understood as exhaustive enumeration but have exemplary character for describing the invention.

The invention is shown in the drawing and is explained in more detail with reference to embodiments.

DESCRIPTION OF THE PREFERRED EMBODIMENT

Figure 1:
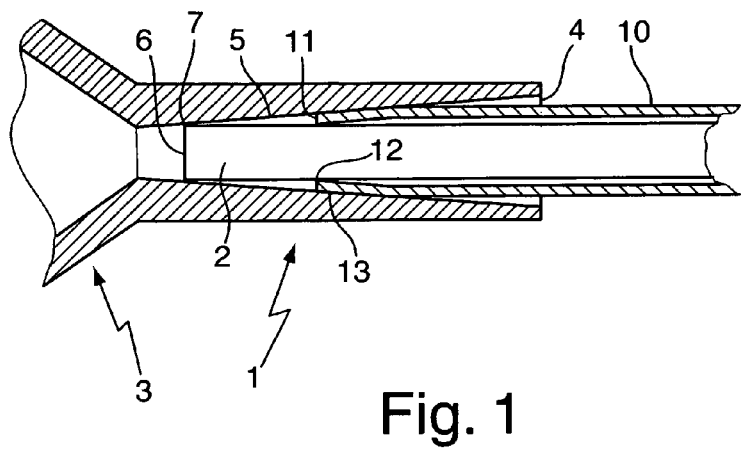
FIG. 1 shows an inventive coupling configuration.

FIG. 1 shows a schematic cross-section through an inventive coupling configuration 1. The coupling configuration 1 comprises a supply capillary 2 and a coupling element 3 (marked with hatched lines) to which the supply capillary 2 is connected, and an envelope capillary 10 which surrounds the supply capillary 2 and is also connected to the coupling element 3.

The coupling element 3 has an opening 4 which merges into a funnel-shaped section 5. The funnel-shaped section 5 conically tapers from the opening 4, wherein the inner diameter linearly decreases with increasing depth (the funnel-shaped section 5 is therefore suitable for clamping a plurality of capillary diameters). Alternatively, the funnel-shaped section may also have a different tapering geometry.

The supply capillary 2 has been inserted and pressed into the funnel-shaped section 5 (in the present case towards the left, into the funnel-shaped section 5) such that an end 6 of the supply capillary 2 is clamped in the funnel-shaped section 5. Pressing-in may be effected e.g. manually. The end 6 of the supply capillary 2 is slightly elastically crimped in the radial direction. The supply capillary 2 is held by friction in the coupling element 3 in the contact area between the end 6 and the funnel-shaped section 5, i.e. at the edge 7 of the end 6. Thus, the edge 7 of the end 6 forms a first holding ring of the supply capillary 2.

An envelope capillary 10 has been pushed over the supply capillary 2 and also inserted and pressed into the funnel-shaped section 5, e.g. also manually. Thus, an end 11 of the envelope capillary 10 is clamped between the supply capillary 2 and the funnel-shaped section 5 of the coupling element 3. The end 11 of the supply capillary 10 is thereby elastically deformed in a radial direction, i.e. compressed. The end 11 thereby exerts a force in a radial inward direction onto the supply capillary 2, thereby frictionally fixing the supply capillary 2 in the contact area 12 between the end 11 and the supply capillary 2 relative to the envelope capillary 10. The end 11 of the envelope capillary 2 continues to exert a force in a radial outward direction onto the funnel-shaped section 5, whereby the envelope capillary 10 is frictionally fixed relative to the funnel-shaped section 5 in the contact area 13 between the end 11 and the funnel-shaped section 5. As a result, the supply capillary 2 is additionally fixed relative to the funnel-shaped section 5 of the coupling element 3 via the contact areas 12 and 13. The contact area 12 forms a second holding ring of the supply capillary 2 in the coupling element 3, which functions indirectly via the contact area 13.

Since the outer diameter of the envelope capillary 10 is larger than the outer diameter of the supply capillary 2, the end 6 of the supply capillary 2 is disposed deeper in the funnel-shaped section 5 (i.e. further away from the opening 4) than the end 11 of the envelope capillary 2. In other words, the end 6 of the supply capillary projects past the end 11 of the envelope capillary. This also causes the first holding ring (at edge 7) to be spaced apart from the second holding ring (at contact area 12), thereby improving the strength of the mounting of the supply capillary 2 in the coupling means 3.

The envelope capillary 10 preferably consists of a material which adheres particularly well to the outer material of the supply capillary 2 and also to the inner material of the funnel-shaped section 5. Rubber is e.g. particularly suited as material for the envelope capillary 10 with respect to fused silica as material of the supply capillary 2 or the funnel-shaped section 5. The material of the envelope capillary 10 can thereby be selected independently of the liquid to be transported.

The supply capillary 2 (and also the envelope capillary 10) can basically be removed from the coupling element 3 towards the right. The required force is much larger than in a coupling configuration without installed envelope capillary.

One further effect of the inventive envelope capillary 10 is the protection of the supply capillary 2. The entirety of envelope capillary 10 and supply capillary 2 is mechanically much more robust than the supply capillary 2 alone. This reduces damage to the supply capillary 2 and therefore expensive repair work. In accordance with the invention, the envelope capillary 10 surrounds parts of the supply capillary 2 within the funnel-shaped section 5 and also at least parts thereof far outside of the funnel-shaped section 5 in order to prevent capillary breakage in the area of capillary mounting, which occurs very often in prior art and entails very expensive repair works.

1/32" PEEK, 450 µm FS (fused silica) or 363 µm FS may e.g. be used as supply capillaries 2. The sizes refer to the outer diameter (OD). Plastic capillaries, e.g. of PEEK, are preferably used as envelope capillaries 10. They are very robust with respect to bending, extension and chemical resistance. The inner diameter of the envelope capillary 10 is preferably only slightly larger than the outer diameter of the supply capillary 2 such that elastic deformation (squeezing) of the envelope capillary 10 can produce a further holding point or holding ring for the supply capillary 2. The outer diameters of the envelope capillary 10 are typically between 100 µm and 1 mm depending on the diameter of the supply capillary 2 and the wall thickness of the envelope capillary 10.

Figure 2:
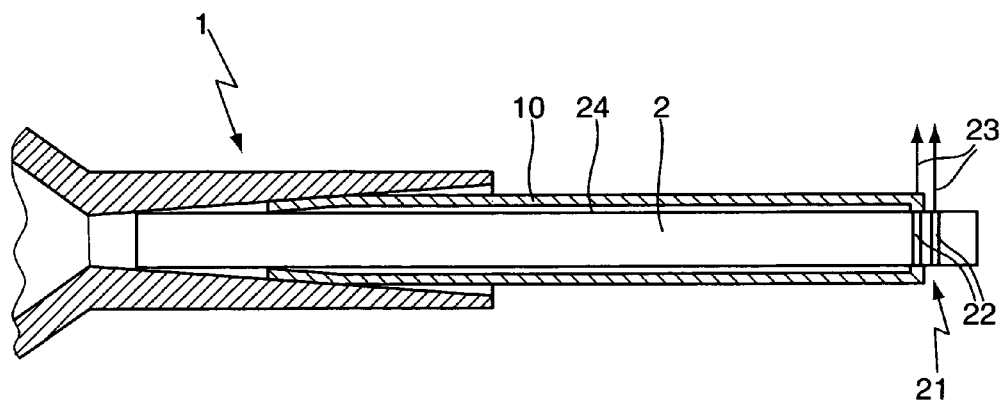
FIG. 2 shows the coupling configuration of FIG. 1 with a leakage sensor.

FIG. 2 shows the coupling configuration 1 of FIG. 1 with an additional leakage sensor 21. The leakage sensor 21 comprises two slightly spaced-apart rings 22 of a metal coating which are disposed on the outer surface of the supply capillary 2. The two rings 22 form a simple capacitor.

When liquid, in particular, the liquid supplied in the supply capillary 2, enters the gap 24 between the supply capillary 2 and the envelope capillary 10 and reaches the leakage sensor 21, the capacitance of the two rings 22 changes. This can be measured by electric contacts 23 of the leakage sensor 21. The associated measuring electronics is not shown in FIG. 2. Therein, the leakage sensor 21 is disposed at an end of the envelope capillary 10. Alternatively, a leakage sensor 21 may be positioned below the envelope capillary 10 independently of the end of the envelope capillary 10, wherein the electric contacts 23 must be guided through the envelope capillary 10.

The leakage sensor 21 can monitor leakages at the transition between the supply capillary 2 and the coupling element 3 as well as the tightness of the supply capillary 2 itself. When the leakage sensor 21 detects a defect, it can be repaired before large amounts of valuable sample substance escape.

Figure 3:
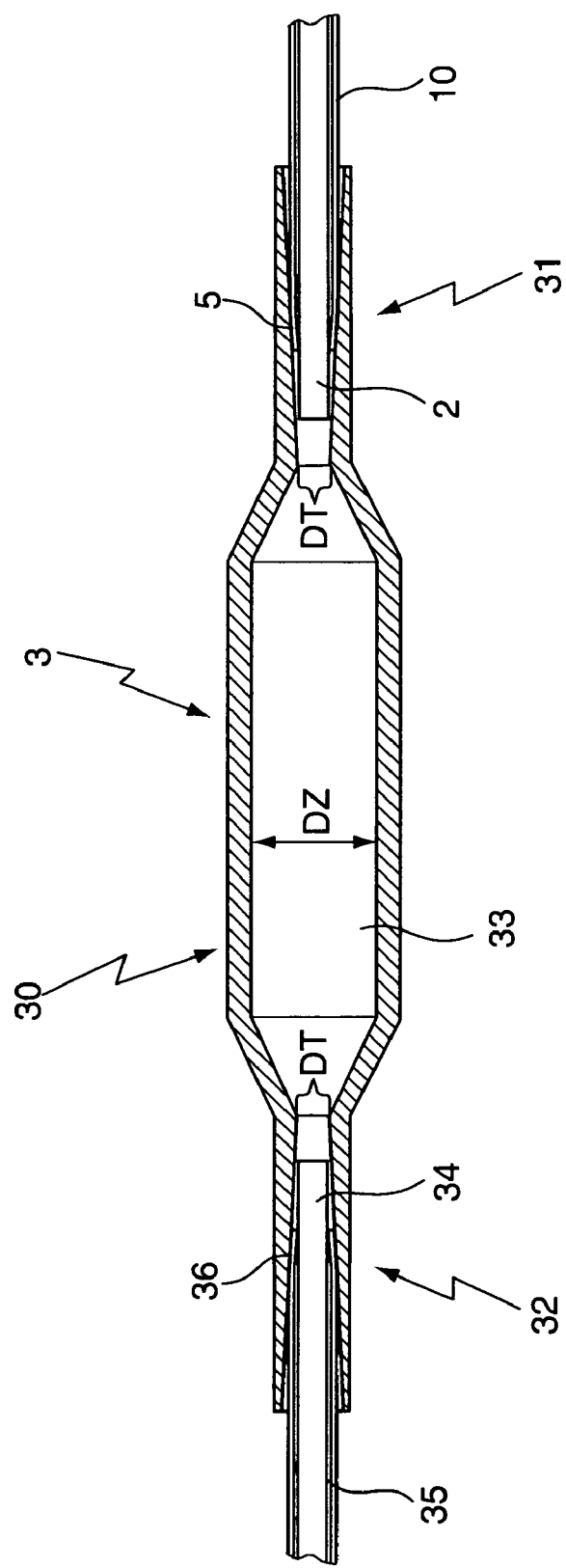
FIG. 3 shows an inventive coupling configuration with cell and connections for two supply capillaries.

FIG. 3 shows a schematic cross-section of an inventive coupling configuration 30 which has two connections 31, 32 for capillaries which are secured in accordance with the invention, and an intermediate cell 33. The coupling configuration 30 has a rotationally symmetric design, in particular, with a substantially circular cylindrical cell 33.

A supply capillary 2 and an envelope capillary 10 are pressed into the funnel-shaped section 5 of the coupling element 3 at the right-hand side connection 31. A further supply capillary 34 and a further envelope capillary 35 are pressed into a further funnel-shaped section 36 of the coupling element 3 at the left-hand side connection 32. The two funnel-shaped sections 5, 36 are disposed coaxially and each terminate in the cell 33 which has a maximum inner diameter DZ which is larger than the smallest inner diameter DT of the funnel-shaped sections 5, 36. Supplied liquid can therefore accumulate in the cell 33, which is wider than the supply capillaries 2, 34 and the funnel-shaped sections 5, 36, e.g. in order to provide a sample amount that is sufficient for spectroscopic measurement.

The coupling configuration 30 of FIG. 3 can also be designated as a press fit cell due to the type of capillary mounting. The inventive press fit cell is particularly suited for use as a measuring cell in NMR spectrometers, wherein the sample substance is transported into the cell via the supply capillaries 2, 34. The inventive press fit connections with supply capillary and safely mounted envelope capillary can also be used in gas chromatography and liquid chromatography in addition to NMR spectroscopy.

Figure 4:
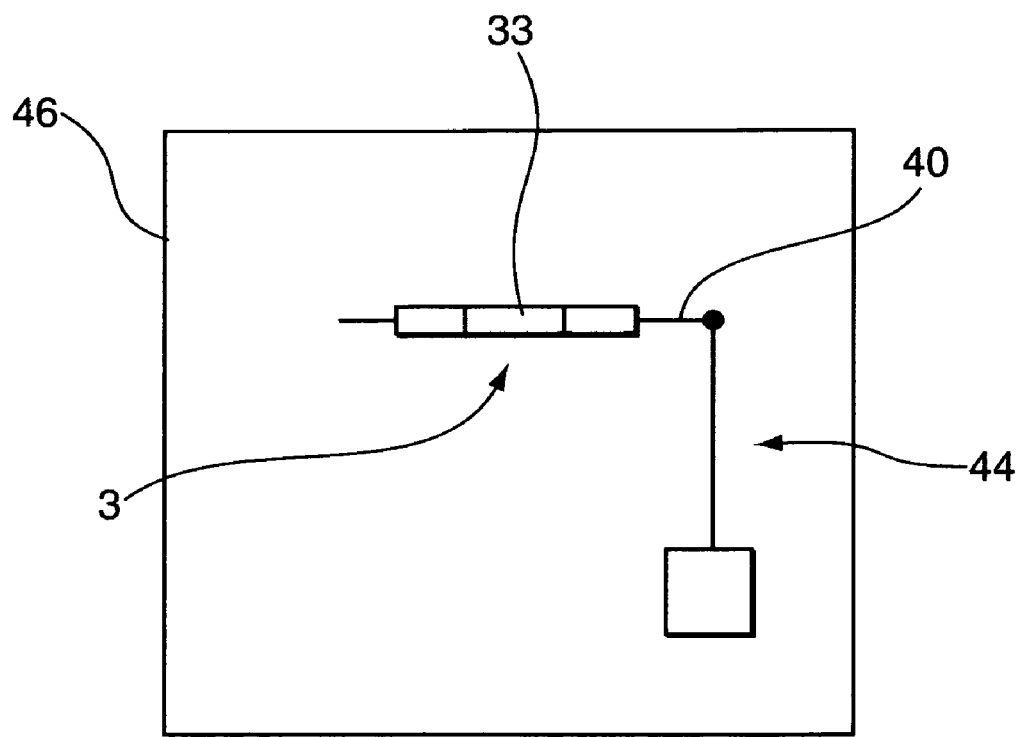
FIG. 4 schematically shows the inventive coupling configuration in use as an NMR measuring cell.

FIG. 4 schematically shows the inventive coupling configuration in use as an NMR measuring cell. Towards this end, the coupling element 3 defines a measuring cell 33 to which a sample can be transported via capillary member 40 with the assistance of transporting means 44. The measuring cell 33 is located within an NMR spectrometer 46 and NMR measurements are performed by the spectrometer 46 on the sample in the measuring cell 33.

We claim:

1. A method for measuring a sample in a nuclear magnetic resonance (NMR) spectrometer, the method comprising the steps of:
   a) preparing a coupling element, the coupling element having a first funnel-shaped section with a first wide opening and a first narrow opening and a second funnel-shaped section with a second wide opening and a second narrow opening, wherein the first and second funnel-shaped sections are coaxial, the coupling element defining a measuring cell disposed between and communicating with the first and second narrow openings of the first and second funnel-shaped sections, the measuring cell having a diameter which exceeds narrowest diameters of the first and second funnel-shaped sections;
   b) inserting a first capillary member through the first wide opening of the first funnel-shaped section, the first capillary member having a first supply capillary and a first envelope capillary disposed about the first supply capillary, first end of the first supply capillary projecting past a first end of the first envelope capillary, wherein the first end of the first supply capillary and the first end of the first envelope capillary are thereby urged against the first funnel-shaped section to clamp, press-fit and seal both the first end of the first supply capillary as well as the first end of the first envelope capillary within the first funnel-shaped section without use of additional auxiliary devices;
   c) inserting a second capillary member through the second wide opening of the second funnel-shaped section, the second capillary member having a second supply capillary and a second envelope capillary disposed about the second supply capillary, a second end of the second supply capillary projecting past a second end of the second envelope capillary, wherein the second end of the second supply capillary and the second end of the second envelope capillary are thereby urged against the second funnel-shaped section to clamp, press-fit and seal both the second end of the second supply capillary as well as the second end of the second envelope capillary within the second funnel-shaped section without use of additional auxiliary devices;

d) transporting a sample substance through the first capillary member and into the measuring cell; and e) carrying out an NMR measurement on the sample substance in the measuring cell.

2. The method of claim 1, wherein said supply capillary consists essentially of fused silica, polyether etherketone (PEEK), or polytetrafluoroethylene (PTFE).

3. The method of claim 1, wherein said supply capillary has an inner diameter of between 50 μm and 500 μm.

4. The method of claim 1, wherein said envelope capillary consists essentially of plastic material or PEEK.

5. The method of claim 1, wherein an outside of said envelope capillary is marked with an indicative color.

6. The method of claim 1, further comprising a leakage sensor monitoring a gap between said supply capillary and said envelope capillary.

7. The method of claim 6, wherein said leakage sensor is disposed between said supply capillary and said envelope capillary.

8. A device for measuring a sample in a nuclear magnetic resonance (NMR) spectrometer, the device comprising:

a coupling element, the coupling element having a first funnel-shaped section with a first wide opening and a first narrow opening and a second funnel-shaped section with a second wide opening and a second narrow opening, wherein the first and second funnel-shaped sections are coaxial, the coupling element defining a measuring cell disposed between and communicating with the first and second narrow openings of the first and second funnel-shaped sections, the measuring cell having a diameter which exceeds narrowest diameters of the first and second funnel-shaped sections;

a first capillary member inserted through the first wide opening of the first funnel-shaped section, the first capillary member having a first supply capillary and a first envelope capillary disposed about the first supply capillary, a first end of the first supply capillary projecting past a first end of the first envelope capillary, wherein the first end of the first supply capillary and the first end of the first envelope capillary are in frictional engagement with the first funnel-shaped section to clamp, press-fit and seal both the first end of the first supply capillary as well as the first end of the first envelope capillary Within the first funnel-shaped section without use of additional auxiliary devices;

a second capillary member inserted through the second wide opening of the second funnel-shaped section, the second capillary member having a second supply capillary and a second envelope capillary disposed about the second supply capillary, a second end of the second supply capillary projecting past a second end of the second envelope capillary, wherein the second end of the second supply capillary and the second end of the second envelope capillary are in frictional engagement with the second funnel-shaped section to clamp, press-fit and seal both the second end of the second supply capillary as well as the second end of the second envelope capillary within the second funnel-shaped section without use of additional auxiliary devices;

means for transporting a sample substance through the first capillary member and into the measuring cell; and means for carrying out an NMR measurement on the sample substance in the measuring cell.

* * * * *